(12) United States Patent
Mastromatteo et al.

(10) Patent No.: US 8,448,494 B2
(45) Date of Patent: May 28, 2013

(54) INTEGRATED ELECTRONIC MICROBALANCE PLUS CHEMICAL SENSOR

(75) Inventors: Ubaldo Mastromatteo, Bareggio (IT); Flavio Francesco Villa, Milan (IT); Gabriele Barlocchi, Cornaredo (IT)

(73) Assignee: STMicroelectronics S.R.L. (IT)

( * ) Notice: Subject to any disclaimer, the term of this patent is extended or adjusted under 35 U.S.C. 154(b) by 656 days.

(21) Appl. No.: 12/648,996

(22) Filed: Dec. 29, 2009

(65) Prior Publication Data

US 2010/0170324 A1    Jul. 8, 2010

(30) Foreign Application Priority Data

Dec. 30, 2008    (IT) ............................... TO2008A1012

(51) Int. Cl.
*G01H 11/08*    (2006.01)
(52) U.S. Cl.
USPC ........... 73/24.06; 73/24.01; 73/23.34; 73/661
(58) Field of Classification Search
USPC .............................. 73/23.34, 24.01, 24.06, 661
See application file for complete search history.

(56) References Cited

U.S. PATENT DOCUMENTS

| | | | | |
|---|---|---|---|---|
| 6,161,420 | A * | 12/2000 | Dilger et al. | 73/24.01 |
| 6,955,787 | B1 * | 10/2005 | Hanson | 422/50 |
| 7,482,737 | B2 * | 1/2009 | Yamada et al. | 310/363 |
| 7,730,785 | B2 * | 6/2010 | Wado et al. | 73/639 |
| 7,874,648 | B2 * | 1/2011 | Matsuda et al. | 347/68 |
| 8,004,021 | B2 * | 8/2011 | Miller et al. | 257/226 |
| 2004/0012463 | A1 | 1/2004 | Kawakubo et al. | |
| 2004/0172798 | A1 | 9/2004 | Ruby et al. | |
| 2006/0125489 | A1 * | 6/2006 | Feucht et al. | 324/633 |

FOREIGN PATENT DOCUMENTS

| | | |
|---|---|---|
| EP | 0822579 | 2/1998 |
| EP | 0992768 | 12/2000 |
| EP | 1291317 | 3/2003 |
| EP | 1324382 | 7/2003 |
| EP | 1577656 | 9/2005 |
| EP | 1719993 | 11/2006 |
| IT | RM2001A000455 | 1/2003 |

OTHER PUBLICATIONS

Cyrano "Nose" the smell of success. NASA Spinoff 2001 (http://www.sti.nasa.gov/tto//spinoff2001/ps4.html).
Gary K. Fedder, et al. Technologies for Cofabricating MEMS and Electronics. Proceedings of the IEEE 96: 306-322 (2008).

(Continued)

*Primary Examiner* — Hezron E Williams
*Assistant Examiner* — Paul West
(74) *Attorney, Agent, or Firm* — Boulware & Valoir (57) ABSTRACT

An electronic microbalance made in a semiconductor body accommodating an oscillating circuit adjacent to a diaphragm. A stack formed by a first electrode, a second electrode, and a piezoelectric region arranged between the first and the second electrode extends above the diaphragm. Any substance that deposits on the stack causes a change in the mass of the microbalance and thus in the resonance frequency of a resonator formed by the microbalance and by the oscillating circuit and can thus be detected electronically. A chemical sensor is obtained by forming a sensitive layer of a material suitable for binding to target chemicals on the stack. The sensitivity of the microbalance can be increased by making the first electrode of molybdenum so as to increase the piezoelectric characteristics of the piezoelectric region.

23 Claims, 6 Drawing Sheets

OTHER PUBLICATIONS

Hisanori Mastumoto, et al., Influence of Underlayer Materials on Preferred Orientations of Sputter-Deposited AlN/Mo Bilayers for Film Bulk Acoustic Wave Resonators. Japanese Journal of Applied Physics 43: 8219-8222 (2004).

Robert Weigel, et al., Microwave Acoustic Materials, Devices, and Applications. IFEE Transactions on Microwave Theory and Techniques 50: 738-749 (2002).

Joel F. Rosenbaum, Bulk Acoustic Wave Theory and Devices, Section 11.7: Composite Resonators. Artech House Inc., Norwood, MA, 1988.

M. Benetti, et al., Chemical Sensor Based-on Thin Film Bulk Acoustic Wave-Resonator (TFBAR). Symposium: Sensors and Microsystems, Feb. 15-17, 2005, Firenze, Italy.

* cited by examiner

INTEGRATED ELECTRONIC MICROBALANCE PLUS CHEMICAL SENSOR

CROSS-REFERENCE TO RELATED APPLICATIONS

This application claims priority to Italian Application No. TO2008A001012 filed on Dec. 30, 2008, incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to an integrated electronic microbalance, in particular an integrated chemical sensor for detecting odorous matters.

BACKGROUND OF THE INVENTION

As is known, the request for microsensors of small dimensions has led to the study of integrated solutions that apply the techniques and know-how acquired in the sector of the manufacture of semiconductors. In particular, integrated sensors for detecting acoustic waves have been studied that use piezoelectric layers, wherein a piezoelectric material layer, arranged between two electrode layers, overlies a cavity and forms an acoustic resonator (see, for example, "Bulk Acoustic Wave Theory and Devices" Joel F. Rosenbaum Artech House Inc., 1988).

These electro-acoustic resonators have been proposed for producing sensors of different types, such as force sensors, pressure sensors, acceleration sensors, weight sensors, and sensors for detecting chemicals, which exploit the variation of the oscillating frequency of the acoustic resonator following a variation of its mass and/or of its geometrical configuration. In practice, the resonator forms an integrated microbalance based upon the piezoelectric effect.

Recently, the use of microbalances as chemical sensors (electronic noses) has awakened particular interest. These sensors find in fact application in the foodstuff sector, where they can be used for controlling the degree of freshness of foodstuffs in the fishery industry (fish, molluscs, etc.), for assessing the degree of seasoning of cheese, for controlling the suitability of packaging, for controlling cooking of foodstuffs, for assessing the quality of beer, liqueurs and spirits. Integrated chemical sensors can moreover be used also in the cosmetics and pharmaceutical industry for controlling perfumes and aromas. The sector of environmental monitoring and that of medicine represent, instead, emerging markets for electronic noses. In both of these last fields they can be used for detecting chemical species produced by bacteria, for example, in environmental applications, for detecting cyanobacteria present in lakes and rivers, or in the medical field for detecting the presence of *Escherichia coli*. Finally, a market that represents an outlet that is very promising from the economic standpoint for electronic noses or, more in general, for automatic gas-detection systems is represented by the automotive sector. In this field, manufacturers are interested in controlling the quality of the air in the passenger compartment of vehicles and in controlling the exhaust gases.

For application as an electronic nose, an apparatus has been proposed that comprises a plurality of quartz chemical sensors, each formed by a quartz region having a surface covered by an adsorbent layer, which is able to bind in a non-selective way with the volatile substances present in the environment (ITRM2001A000455). In practice, the quartz forms, with an associated oscillating circuit, an electrical resonator having a natural resonance frequency comprised between 1 MHz and 20-30 MHz. Each sensor is provided with a different adsorbent layer. When the chemical substances in the environment (analytes) are adsorbed by one or more chemical sensors, the latter increase in weight, varying their own masses, and thus their own oscillating frequency. Alternatively, the relaxation time of the oscillations is measured.

A processing electronics connected to the chemical sensors processes the generated signals and compares them with known configurations in order to recognize the chemicals.

Known quartz sensors may, however, undergo improvement, in particular as regards sensitivity and the overall dimensions, which do not enable use thereof in many applications. The use of quartz renders moreover production complex and burdensome.

Sensors on silicon substrates have moreover been proposed, having cavities obtained by "bulk micromachining" using tetramethyl-amonium hydroxide (TMAH) (see for example "Sensors and Microsystems: Proceedings of the 10th Italian Conference" A. G. Mignani, R. Falciai, C. Di Natale, A. D'Amico, World Scientific Publishing Company, July 2008). This solution envisages deposition, on a surface of a silicon wafer, of a silicon nitride layer, operating as an etch stop, a first aluminium layer (bottom electrode), an aluminium nitride layer (piezoelectric material), and a second aluminium layer (second electrode). Then, an anisotropic back etching is performed, which is stopped on the silicon nitride layer, and the wafer is diced. In each die thus obtained, the stack of layers on the front defines a diaphragm, whereon a thin layer of a sensitive material, such as porphyrin, is deposited.

In this process, the required type of machining is costly and the use of TMAH is not usual in present production lines for integrated circuits. In addition, the etching procedure causes the formation, in the substrate, of a cavity with a trapezium cross-section having a minor base formed by the diaphragm and sides inclined by 45°-50°. Given that the thickness of the substrate is generally 675-700 μm, the major base of the cavity occupies an area having a side or diameter of 1.2-1.4 mm added to the width of the diaphragm. The minimum total area required by each microbalance is thus much greater than that due to the oscillating region alone. The microbalance thus has large overall dimensions, which reduces the possibility of integration thereof.

Consequently, in general, the known sensors do not provide the desired sensitivity, involve complex manufacturing processes, present high costs and dimensions such as not to enable a wide application thereof.

SUMMARY OF THE INVENTION

The aim of the present invention is to provide a microbalance structure that overcomes one or more of the drawbacks of the known art.

An electronic microbalance comprises a body of semiconductor material; an electronic high-frequency circuit integrated in the body; a diaphragm arranged laterally to the electronic high-frequency circuit; a first electrode arranged above the diaphragm; a second electrode arranged above the first electrode; and a piezoelectric region, arranged between the first and second electrodes.

A process of manufacturing a microbalance comprises the steps of providing a wafer of semiconductor material having a surface; integrating an electronic circuit in the wafer; forming a diaphragm laterally to the electronic circuit; forming a first electrode above the diaphragm; forming a piezoelectric region on the first electrode; and forming a second electrode above the piezoelectric region.

BRIEF DESCRIPTION OF THE DRAWINGS

For a better understanding of the present invention, preferred embodiments thereof are now described, purely by way of non-limiting example, with reference to the attached drawings, wherein.

DETAILED DESCRIPTION OF THE INVENTION

Figure 1:
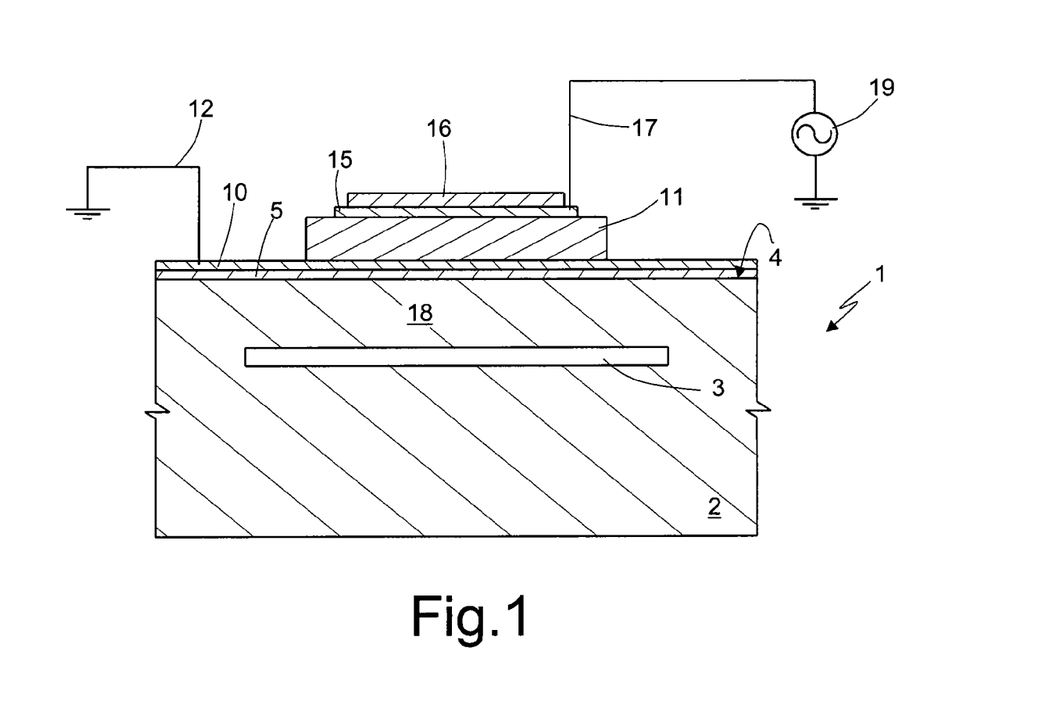
FIG. 1 is a cross-section of a silicon wafer integrating an embodiment of the present electronic microbalance.

FIG. 1 shows a microbalance 1 integrated in a body 2 of semiconductor material, for example, monocrystalline silicon, and having a buried cavity 3, which delimits at the bottom a diaphragm 18, which is also of monocrystalline silicon.

A buffer layer 5, for example, of aluminium nitride (AlN), extends above the diaphragm 18, and a bottom electrode 10, for example, of molybdenum, extends on the buffer layer 5. In the embodiment considered, the buffer layer 5 has a thickness comprised between 30 and 100 nm, for example 50 nm, and the bottom electrode 10 has a thickness of 50-150 nm, for example 100 nm.

A piezoelectric region 11 extends on the bottom electrode 10 and has here an area smaller than the electrode 10 so as to enable electrical connection of the bottom electrode 10, as represented by the wire 12, to a ground potential. The piezoelectric region 11 has a thickness of 1-3 μm, for example, approximately 2 μm.

A top electrode 15, which is, for example, also of molybdenum and has a thickness of 50-150 nm, for example, 100 nm, extends on the piezoelectric region 11. The top electrode can have the same area as, or an area smaller than, the piezoelectric region 11 and is connected, for example, via a wire 17 to an oscillator 19, of a known type and not shown in detail.

Finally, a supporting region 16 extends on the top electrode 15. If the microbalance 1 forms a chemical sensor, the supporting region 16 is a sensitive region of a material such as to bind with the chemical to be detected, in particular, a metal-porphyrin having affinity with this chemical.

Operation of the microbalance 1 of FIG. 1 is illustrated hereinafter. The circuit formed by the piezoelectric region 11 and by the oscillator 19 forms an electrical resonator having a natural oscillation frequency. When a mass is deposited on the supporting region 16 or an analyte binds thereto, the resonator undergoes a variation of the oscillating frequency Δf according to the Sauerbray equation:

$$\Delta f = -\frac{2f_o^2}{A\sqrt{\mu\rho}}\Delta m \qquad (1)$$

where Δm is the mass variation, $f_o$ is the natural oscillation frequency of the resonator, μ is the shear modulus, ρ is the density, and A is the area of the oscillating surface (area of the base of the parallelepiped or in general of the solid formed by the piezoelectric region 11).

The microbalance 1 has a high sensitivity, thanks to its reduced dimensions and to its structure, obtainable by virtue of the microelectronic techniques.

The sensitivity S of the balance 1 can be calculated as:

$$S = \frac{\Delta f}{\Delta m} = -\frac{2f_o^2}{A\sqrt{\mu\rho}} \qquad (2)$$

The microbalance 1 of FIG. 1 can be made using the technique described in EP-A-1 324 382, for manufacturing an SOI wafer, and the process described in EP-A-1577656, for manufacturing a pressure sensor.

Figure 2:
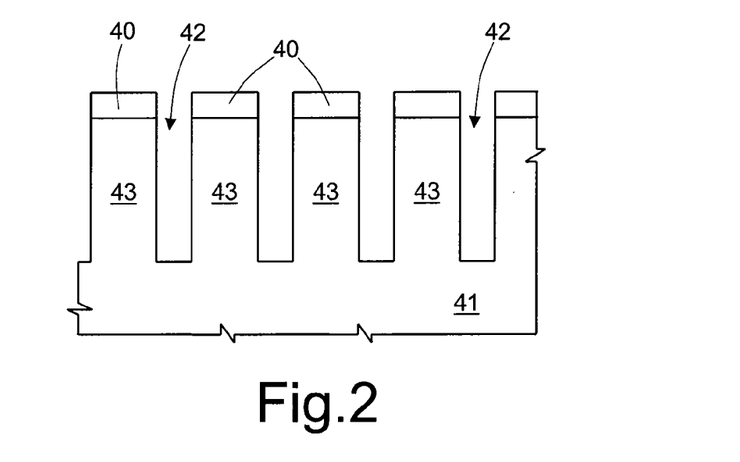
FIG. 2 shows a cross-section of a semiconductor substrate, in a manufacturing step of the microbalance of FIG. 1.
Figure 3:
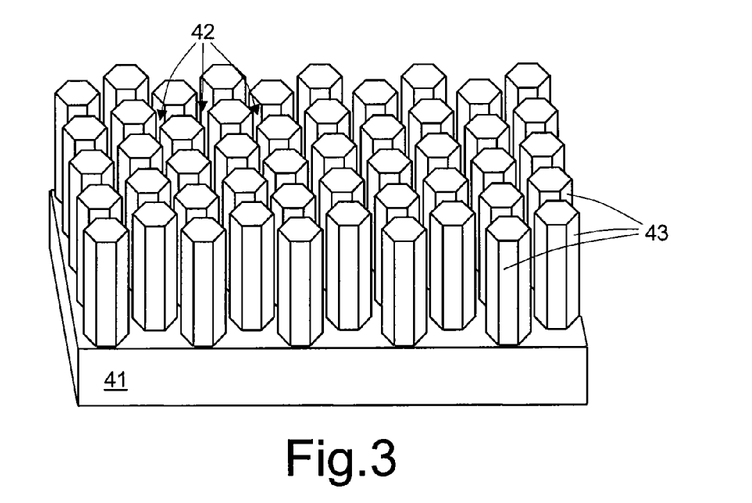
FIG. 3 is a perspective view of the structure of FIG. 2.

Initially (FIG. 2), using a mask 40, a dry anisotropic chemical etching is carried out of a substrate 41 of semiconductor material, for example silicon, so as to form a plurality of trenches 42 having a width of, for example, 1 μm, which communicate with one another and delimit a plurality of columns 43 having a substantially hexagonal cross-section, as may be seen in FIG. 3. For example, the trenches can have a depth of 11 μm±1 μm, and the columns 43 can have a diameter of 2 μm.

Next, an epitaxial growth is performed in a known way. Consequently, an epitaxial layer 44 grows above the columns 43 and closes the trenches 42 at the top.

A thermal annealing is then performed, for example for 25-30 minutes at approximately 1200° C., preferably in hydrogen atmosphere. Alternatively, nitrogen can be used, with longer times and using protection layers.

Figure 4:
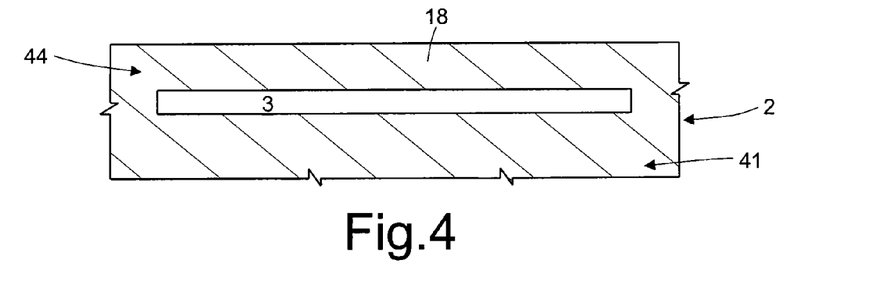
FIG. 4 shows a cross-section of the semiconductor substrate of FIG. 2, in a successive manufacturing step.

As discussed in the aforementioned patent applications, the annealing causes a migration of the silicon atoms, which tend to go into a lower-energy configuration. Consequently, by suitably selecting the width of the trenches 42, it is possible to cause the silicon atoms to migrate completely from the portions of the columns 43, forming the buried cavity 3, as shown in FIG. 4. A silicon layer remains on the buried cavity 3 and has a thickness of, for example, 20 μm, formed in part by silicon atoms grown epitaxially and in part by silicon atoms that have migrated and form the diaphragm 18. The body 2 is thus formed.

On a wafer thus obtained, after the possible integration of electronic components 38 (FIG. 5) of the oscillator and of the other associated electronic circuits, the buffer layer 5 is deposited, preferably by RF sputtering. The buffer layer 5, for example of AlN, has the aim of optimizing the quality of the molybdenum layer forming the bottom electrode 10 and consequently the subsequent growth of the piezoelectric layer intended to form the piezoelectric regions 11. The buffer layer 5 can be left over the entire surface 4 of the wafer, at least in the area of the microbalances, or defined so as to form a plurality of buffer regions 5, one for each microbalance 1.

Next, a first electrode layer is deposited. For example, molybdenum is deposited. The use of molybdenum has proven particularly advantageous for the performance of the microbalance 1. In fact, the intensity of the piezoelectric effect of a given piezoelectric layer is the greater the more the piezoelectric layer is oriented along the crystallographic axis, perpendicular to the plane of growth. Markedly oriented polycrystalline piezoelectric layers have piezoelectric properties similar to those of the epitaxial layers, with the advantage that they can be deposited at lower temperatures. Studies conducted by the present applicant have shown that molybdenum is more effective than aluminium for forming piezoelectric layers of AlN that are markedly oriented along the axis c; thus the use of the indicated materials contributes to obtaining a high sensitivity of the microbalance 1.

The first electrode layer can coat the entire surface of the wafer, at least in the area of the microbalances 1, since it defines a ground electrode, common to all, and can possibly be used as level metallization for the associated circuitry, connected to the standard aluminium tracks.

Next, a piezoelectric layer, preferably AlN, is deposited by sputtering and defined so as to obtain one piezoelectric region 11 for each microbalance 1. Alternatively, it is possible to have a piezoelectric layer not defined, common to all the microbalances 1 so as to prevent the presence of a step during deposition of the subsequent top-electrode layer. After deposition, the top-electrode layer, preferably of molybdenum, is defined via current photolithographic techniques so as to form the top electrode 15, one for each microbalance 1.

As an alternative to the above, it is possible to define the layers of the top and bottom electrodes and the piezoelectric layer in sequence, only after depositing the top-electrode layer.

Finally, the sensitive region 16, for example, an appropriate metal-porphyrin, according to the chemical to be detected, is deposited on the top electrodes 15, for example by "spotting", so as to obtain the structure of FIG. 1. In addition, a passivation layer (not shown) may be deposited and opened for forming contacts (not shown).

Figure 5:
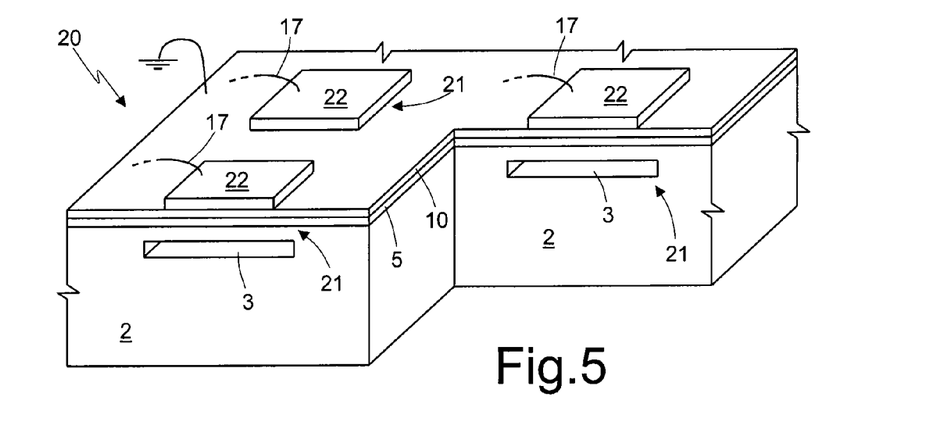
FIG. 5 is a partially sectioned perspective view of a sensor formed by a plurality of microbalances of FIG. 1.

The microbalance 1 of FIG. 1 can be integrated in a same chip with other microbalances 1 sensitive to other chemicals. FIG. 5 shows, for example, a chip 20, which integrates a plurality of chemical sensors 21, for example eight (only three whereof are visible). The chemical sensors 21 have the structure shown in FIG. 1 and are represented schematically, with a surface region 22 representing the set of the regions 11, 15 and 16. In the shown embodiment, the bottom electrode 10 covers all the surface shown of the chemical sensors 21 area, and the wires 17 are connected to appropriate external areas. Alternatively, the bottom-electrode layer 10 can be defined so as to form contact pads and interconnection lines to the associated circuitry (FIG. 6).

In practice, the chemical sensors 21 are arranged in an array and are for example made so as to bind to different chemicals; the different signals generated can then be used and compared with known distributions for recognition of chemical substances.

Figure 6:
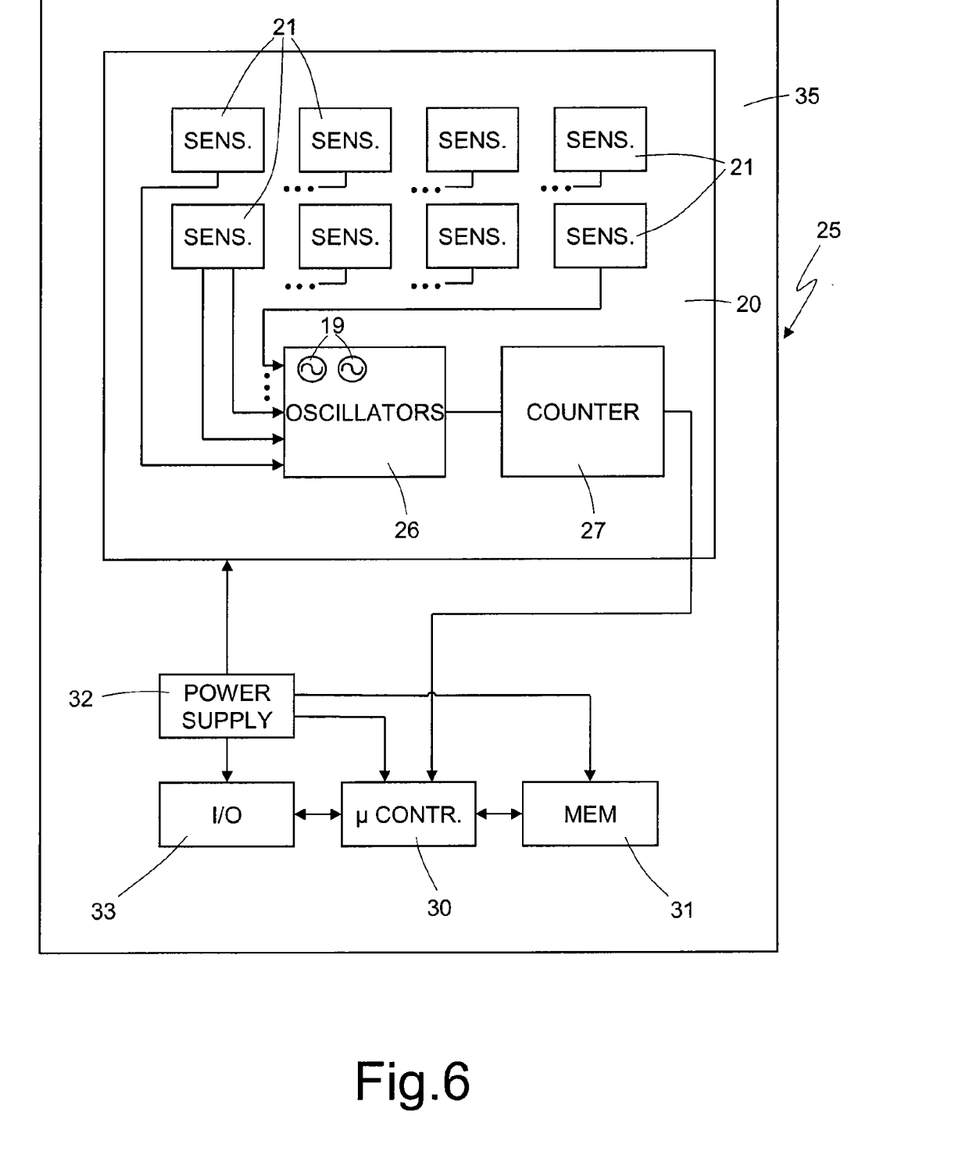
FIG. 6 is a block diagram of an apparatus for detecting chemical substances.

FIG. 6 shows, for example, an apparatus for recognition of odours or "electronic nose" 25 comprising a board 35, carrying the chip 20, which integrates an array of eight chemical sensors 21, and an associated electronics, which includes an oscillator stage 26, including a plurality of oscillators 19, one for each microbalance 21, and a converter 27, for example a counter. The oscillator stage 26 drives the array of chemical sensors 21 and generates a plurality of periodic signals (pulse trains) having a frequency equal to the frequency f of the resonators. The counter 27 counts the number N of pulses within a fixed time interval T and generates digital signals that encode their oscillation frequencies f, the value whereof depends upon the possible bond with respective analytes bound thereto.

The output of the chip 20 is connected to a microcontroller 30 connected to a memory 31, for example, of an EEPROM type, to a power-supply stage 32 and to an input/output stage 33, for example for displaying the results. The microcontroller 30 is then able to detect the possible differences of frequency $\Delta f$ for each chemical sensor 21 and, according to patterns stored in the memory 31, to recognize the chemicals present in the environment.

The odour-recognition apparatus 25 can be housed in an external casing so as to protect the chemical sensors 21. In this case, it can be provided with pneumatic actuators and corresponding input/output connectors, valves and control stages, for introducing and venting the gases to be analysed, as well as possibly input/output stages and electrical connectors towards an external personal computer (PC).

Figure 7:
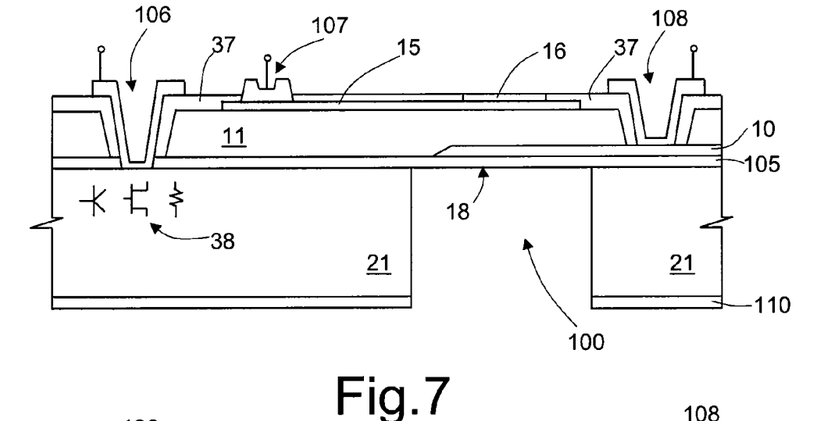
FIGS. 7-9 are different embodiments of the instant microbalance.

FIG. 7 shows an embodiment of a detector wherein the cavity underlying the diaphragm is not buried. In detail, here the substrate 2 has a trench 100 obtained using the technique of bulk micromachining by selectively removing a portion of the silicon substrate 2 from the back using a reactive ion etching plasma tool. A dielectric layer 105, e.g., thermally grown silicon dioxide, extends on the surface of the substrate 2 and defines the diaphragm 18. A protection or passivation layer 37 extends on the surface of the microbalance 1, except at the sensitive region 16 and at contacts 106-108. The protection layer 37 may be SiN and the supporting region 16 may not be present. A circuitry 38 extends laterally to the microbalance area; the contacts 106-108 connect the circuitry 38, the bottom electrode 10 and the upper electrode 15 to the other components of the "electronic nose" 25 of FIG. 6. Here, the substrate 2 is a standard substrate having a thickness of 725 μm and a thermal oxide 110 having a thickness of 1 μm extends on the bottom surface of the substrate 2.

The substrate 2 has here a trench 100 for each microbalance 1.

Figure 8:
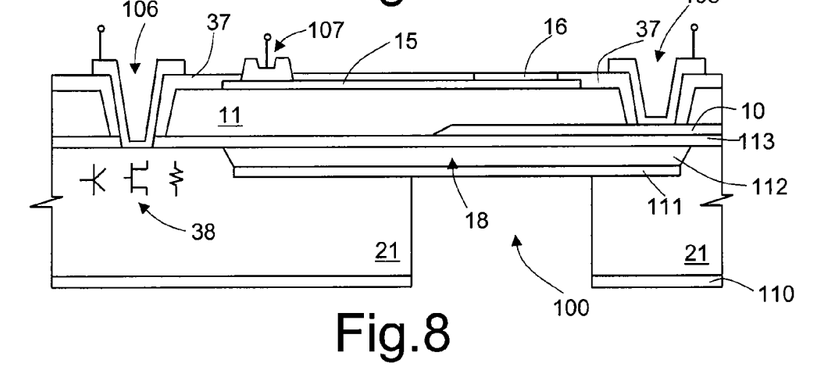

In FIG. 8, the diaphragm 18 is formed by a multilayer including a bottom dielectric region 111 (e.g., of silicon dioxide), a polysilicon portion 112 and an upper dielectric layer 113 (e.g., of silicon dioxide). Such a structure may be obtained, before forming the components of the circuitry 38, during the epitaxial growth. In detail, before growing an epitaxial layer, the bottom dielectric region 111 is thermally grown or deposited on the sensing portions of the wafer, so that during the epitaxial growth, the polysilicon portion 112 grows over the bottom dielectric region 111. Elsewhere, the epitaxial layer is monocrystalline, to allow integration of electric components. Then, after the integration of the circuitry 38, the upper dielectric layer 113 is grown or deposited and covers the entire surface of the substrate 2. In the alternative, the bottom dielectric layer 111 and the polysilicon layer 112 may be grown or deposited on the upper surface of the substrate 2, before or after forming the components of the circuitry 38.

Figure 9:
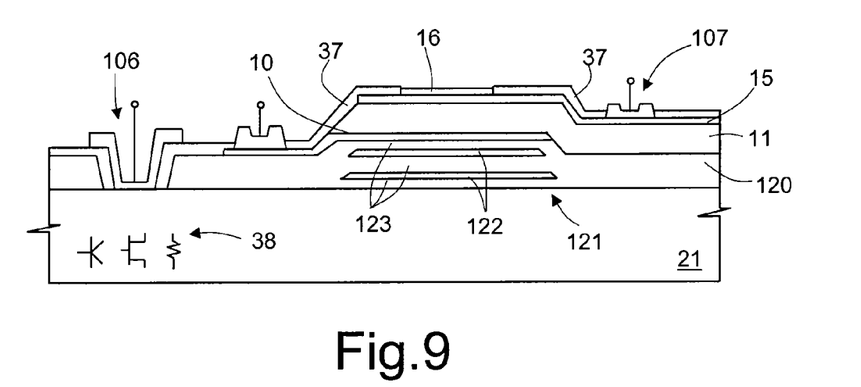

FIG. 9 is an embodiment wherein the detector uses the reflecting ability of a Bragg mirror to contain the acoustic waves in the overlying piezoelectric region 11 and thus is functionally equivalent to the buried cavity 3 or the trench 100. In detail, here, the substrate 2 is covered by a thick dielectric layer 120 which, in each sensor portion thereof, accommodates a mirror 121. The mirror 121 is formed by a stack of alternating high acoustic impedance layers 122 and low acoustic impedance layers 123 as described, e.g., in U.S. Pat. Nos. 6,448,695 or 6,933,807, As an example, the low acoustic impedance layers 123 may be of silicon dioxide and the high acoustic impedance layers 122 may be of tungsten.

Figure 10A:
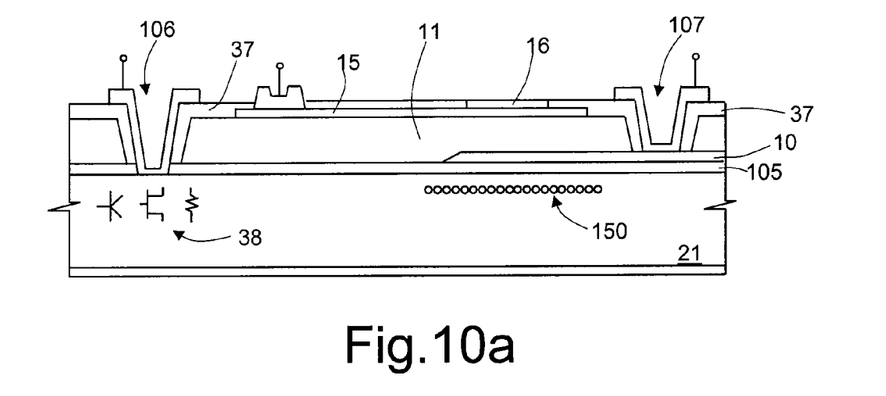
FIGS. 10a and 10b show a different embodiment of the present microbalance, in two subsequent manufacturing steps.
Figure 10B:
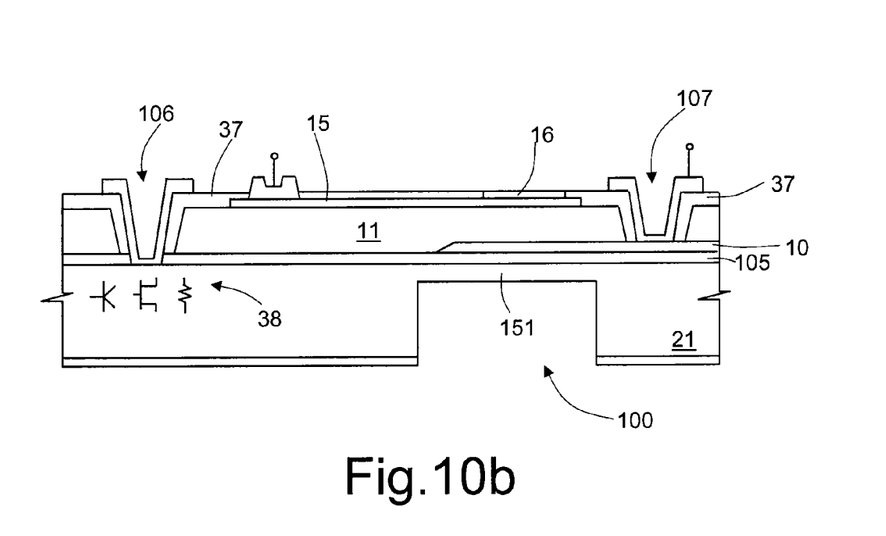

FIGS. 10*a* and 10*b* refer to an embodiment wherein the cavity 100 is not obtained by bulk micromachining, but by using the process described in U.S. Pat. No. 7,294,536 or in U.S. Pat. No. 7,071,073, In particular, before forming the components of the circuitry 38, a buried oxide layer 150 is formed in the substrate 2, FIG. 10*a*. At the end of the process, after forming the circuitry 38 and the microbalance regions 10, 11, 15, 16, 37 on the surface of the substrate 2, the substrate 2 is etched from the back to selectively remove silicon using, e.g., a reactive ion etching plasma tool, until reaching the buried oxide layer 150. The buried oxide layer 150 is removed as well, forming the cavity or trench 100 under a silicon layer 151 under the substrate upper surface. The remaining portion of the substrate 2 over the trench 100 forms a diaphragm 152. Here, the substrate 2 may have a thickness of 308 μm.

Figure 11:
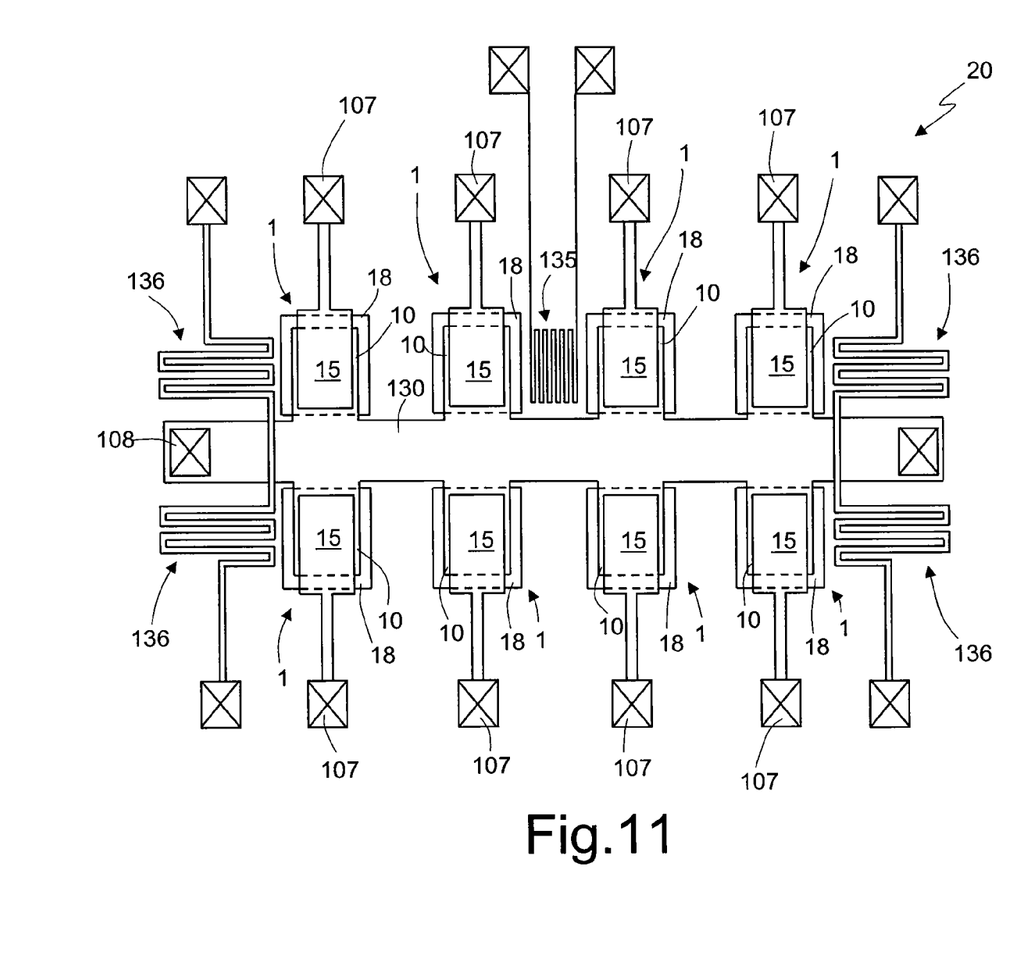
FIG. 11 shows a top view of an embodiment of the present electronic microbalance.

In an embodiment, an integrated heater is formed using the aluminum metallization, as shown in the layout of FIG. 11, relative to the microbalance area. Here, the chip 20 comprises eight microbalances 1 made according to any of FIGS. 1, 7-10. Each microbalance 1 has its own top electrode 15 connected to an contact 107 and overlying a diaphragm 18, each defined by an underlying cavity 3 or trench 100 or Bragg mirror 121. The bottom electrodes 10 of the microbalances 1 are connected together through a connecting line 130 connected to contacts 108. At least one heater 135 is formed in the microbalance area, e.g. in a central portion thereof. The heater 135 is for example formed of an aluminum coil, in the same metal level as the contacts 107-108. Temperature sensors 136 are also formed laterally to the microbalances area. They may also be formed of aluminum, in the same metal level as the heater 135. Thereby, forming the heater and the temperature sensors 136 does not require additional masks.

The presence of a heater and a temperature control (including the temperature sensors 136) allows a reduction in the cleaning times of the microbalances 1. In fact, after each olfactory operation, the microbalances 1 are to be brought back to the starting conditions, by cleaning the chemically interactive materials, e.g. the metal-porphyrins. This operation is generally performed by causing dry air to flow on the chemically interactive materials. The presence of heaters allows a heating of the flowing air, helping the "desorption" processes and thus releasing of the substances adsorbed during the previous olfactory operation. To this end, the apparatus may comprise electric controlled valves that allow introduction of a stream of gas or air to be sensed, and then introduction of a cleaning and calibration stream of air, to reset the initial conditions.

Thereby, the costly Peltier cell can be eliminated, and the apparatus may have much lower cost, smaller dimensions and reduced weight.

The microbalance described herein has numerous advantages.

In particular, it has a high sensitivity, thanks to its integration in an integrated device of small dimensions, and to the use of molybdenum in contact with the piezoelectric region 11.

The definition of the diaphragm 18 by means of the buried cavity 3 causes the area of the microbalance to correspond substantially to that of the buried cavity. Consequently, the microbalance 1 has small dimensions, which enable integration of a number of microbalances and possibly of the driving and control circuits in a same chip.

The integration of a heater 135 and any temperature sensor in the chip 20 allows the obtainment of a detecting device of very small dimensions (pocket size), low weight, small power consumption, low cost. Thus, the device may be mounted in portable apparata, such as a cell phone, and may be easily connected to an external unit (e.g., a portable computer) for data processing.

Finally, it is clear that modifications and variations can be made to the microbalance described and illustrated herein, without thereby departing from the scope of the present invention, as defined in the attached claims.

For example, part of the electronics for processing the digital electrical signals provided by the converter can be integrated in the same chip as the sensors.

What is claimed is:

1. An electronic microbalance, comprising:
   a body of semiconductor material;
   an electronic oscillating circuit integrated in the body;
   a diaphragm arranged laterally to the electronic oscillating circuit;
   a first electrode arranged above the diaphragm;
   a second electrode arranged above the first electrode;
   a piezoelectric region, arranged between said first and second electrodes;
   a heater extending laterally to the first and second electrodes; and
   a plurality of metal contacts in direct electric contact with the electronic oscillating circuit and the first and the second electrodes;
   wherein said heater is formed in a same metal level as the metal contacts.

2. The microbalance according to claim 1, wherein the body houses a buried cavity underneath and delimiting a bottom surface of the diaphragm, the diaphragm being a portion of the body.

3. The microbalance according to claim 1, wherein the body has a back surface and accommodates a trench extending from the back surface and delimiting the diaphragm.

4. The microbalance according to claim 3, wherein the diaphragm comprises a dielectric layer extending on the body.

5. The microbalance according to claim 1, wherein the diaphragm is delimited by a Bragg mirror, including a stack of high and low acoustic impedance layers.

6. The microbalance according to claim 1, wherein said first electrode is of molybdenum.

7. The microbalance according to claim 1, wherein said second electrode is of molybdenum.

8. The microbalance according to claim 1, wherein the electronic oscillating circuit comprises an oscillator connected to said piezoelectric region through said first and second electrodes, said oscillator forming, with said piezoelectric region, a resonant circuit.

9. The microbalance according to claim 1, comprising a buffer layer extending between said body and said first electrode.

10. The microbalance according to claim 9, wherein the piezoelectric region and the buffer layer are of aluminium nitride.

11. The microbalance according to claim 1, forming a chemical sensor and further comprising a sensitive layer arranged above said second electrode, of a material such as to bind with target chemical substances.

12. The microbalance according to claim 1, further comprising a temperature sensor arranged laterally to the first and second electrodes and formed in the same metal level as the heater.

13. An integrated device for detecting chemicals, comprising:
- a body of semiconductor material;
- an electronic oscillating circuit integrated in the body;
- a plurality of microbalances arranged laterally to the electronic oscillating circuit, each microbalance comprising a diaphragm, a first electrode arranged above the diaphragm, a second electrode arranged above the first electrode, and a piezoelectric region, arranged between said first and second electrodes;
- a heater extending laterally to the first and second electrodes; and
- a plurality of metal contacts in direct electric contact with the electronic oscillating circuit and the first and the second electrodes;
    - said heater being formed in the same metal level as the metal contacts.

14. An apparatus for detecting chemical substances, comprising:
- a body of semiconductor material;
- an electronic oscillating circuit integrated in the body;
- a plurality of microbalances arranged laterally to the electronic oscillating circuit, each microbalance comprising a diaphragm, a first electrode arranged above the diaphragm, a second electrode arranged above the first electrode, and a piezoelectric region, arranged between said first and second electrodes, a processing unit, connected to said microbalances;
- a heater extending laterally to the first and second electrodes;
- a plurality of metal contacts in direct electric contact with the electronic oscillating circuit and the first and the second electrodes;
    - said heater being formed in the same metal level as the metal contacts; and
- a configuration memory, connected to said processing unit and storing a plurality of frequency data associated to target chemical substances.

15. A process of manufacturing a microbalance, comprising the steps of:
- providing a wafer of semiconductor material having a body and a surface;
- integrating an electronic oscillating circuit in the wafer;
- forming a diaphragm laterally to the electronic oscillating circuit;
- forming a first electrode above the diaphragm;
- forming a piezoelectric region on the first electrode;
- forming a second electrode above the piezoelectric region;
- depositing a metal layer; and,
- defining said metal layer to simultaneously form a heater extending laterally to the microbalance and metal contacts, wherein said heater is in direct electric contact with said electronic oscillating circuit and said first and second electrodes.

16. The process according to claim 15, wherein at least one between said first and second electrodes is of molybdenum.

17. The process according to claim 15, comprising connecting the oscillating circuit to the piezoelectric region.

18. The process according to claim 15, comprising forming a buffer layer of aluminium nitride above said body, underneath said first electrode.

19. The process according to claim 15, forming a chemical sensor including a sensitive layer arranged above said second electrode, of a material such as to bind with target chemical substances.

20. A process according to claim 15, wherein forming a diaphragm comprises forming a buried channel in the body.

21. A process according to claim 15, wherein forming a diaphragm comprises forming a dielectric layer on the body, under the first electrode, and selectively removing a portion of the body under the dielectric layer and the first electrode.

22. A process according to claim 15, wherein forming a diaphragm comprises forming, under the first electrode, a Bragg mirror including a stack of high and low acoustic impedance layers.

23. A process according to claim 15, wherein forming a diaphragm comprises, before forming the first electrode, forming a buried oxide layer, and, after forming the second electrode, selectively removing a portion of the body under the buried oxide layer and removing the buried oxide layer.

* * * * *